(12) United States Patent
Banna et al.

(10) Patent No.: US 10,713,936 B2
(45) Date of Patent: Jul. 14, 2020

(54) PAIRING OR ASSOCIATING ELECTRONIC DEVICES

(75) Inventors: Rami Banna, Paddington (AU); Justin Gilmour, Camperdown (AU); Werner Meskens, Opwijk (BE); Brian Gordon, Chatswood (AU)

(73) Assignee: Cochlear Limited, Macquarie University, NSW (AU)

( * ) Notice: Subject to any disclaimer, the term of this patent is extended or adjusted under 35 U.S.C. 154(b) by 642 days.

(21) Appl. No.: 13/882,456

(22) PCT Filed: Oct. 26, 2011

(86) PCT No.: PCT/IB2011/002545
§ 371 (c)(1),
(2), (4) Date: Jun. 18, 2013

(87) PCT Pub. No.: WO2012/056298
PCT Pub. Date: May 3, 2012

(65) Prior Publication Data
US 2013/0265144 A1    Oct. 10, 2013

(30) Foreign Application Priority Data
Oct. 29, 2010  (AU) .............................. 2010904833

(51) Int. Cl.
*G08C 17/02* (2006.01)
*A61N 1/372* (2006.01)
(Continued)

(52) U.S. Cl.
CPC ......... *G08C 17/02* (2013.01); *A61N 1/37217* (2013.01); *H04R 25/554* (2013.01);
(Continued)

(58) Field of Classification Search
CPC ................ G08C 17/02; A61N 1/37217; A61N 1/36032; A61N 1/37252
See application file for complete search history.

(56) References Cited

U.S. PATENT DOCUMENTS 6,067,474 A * 5/2000 Schulman ................ A61N 1/08
607/57
2001/0031909 A1* 10/2001 Faltys ................ A61N 1/37217
600/25
(Continued)

FOREIGN PATENT DOCUMENTS

JP   2000-287299      10/2000
WO   2010/108492 A1   9/2010

OTHER PUBLICATIONS

Specification of the Bluetooth System Feb. 22, 2001.*
(Continued)

*Primary Examiner* — Nabil H Syed
(74) *Attorney, Agent, or Firm* — Pilloff Passino & Cosenza LLP; Martin J. Cosenza

(57) ABSTRACT

A system that includes an implanted medical device such as an auditory prosthesis having a capacity to conduct communications on two channels to establish an association for communication with another electronic device. One of the channels is preferably a short range or near field channel, and the other channel is a broadcast channel. A method of asynchronous communication using both channels for establishing the association is also described.

24 Claims, 6 Drawing Sheets

(51) Int. Cl.
*H04R 25/00* (2006.01)
*A61N 1/378* (2006.01)
*A61N 1/36* (2006.01)

(52) U.S. Cl.
CPC ........ *A61N 1/36036* (2017.08); *A61N 1/3787* (2013.01); *A61N 1/37252* (2013.01); *H04R 25/552* (2013.01); *H04R 25/558* (2013.01); *H04R 2225/67* (2013.01)

(56) References Cited

U.S. PATENT DOCUMENTS

| | | | |
|---|---|---|---|
| 2006/0161223 A1* | 7/2006 | Vallapureddy et al. | ........ 607/60 |
| 2007/0147641 A1 | 6/2007 | Platz | |
| 2008/0009253 A1 | 1/2008 | Callias et al. | |
| 2008/0085023 A1 | 4/2008 | Kulkarni et al. | |
| 2009/0010465 A1 | 1/2009 | Boguslavskij et al. | |
| 2009/0067653 A1* | 3/2009 | Meskens | ............... H04R 25/552 381/315 |
| 2010/0030012 A1* | 2/2010 | Meskens | ........................ 600/25 |
| 2010/0046779 A1* | 2/2010 | Crawford | ............... H04R 25/00 381/328 |
| 2010/0167643 A1 | 7/2010 | Hirsch | |
| 2010/0291880 A1* | 11/2010 | Feldstein | ........................ 455/73 |
| 2011/0176686 A1* | 7/2011 | Zaccaria | ......................... 381/60 |
| 2011/0275316 A1* | 11/2011 | Suumaki | ............ G06K 7/10237 455/41.1 |

OTHER PUBLICATIONS

International Search Report and Written Opinion for PCT/IB2011/002545 dated May 7, 2012, 11 pages.
Supplementary Extended European Search Report for EP Application No. 11 835 702.9, dated Oct. 25, 2016.

* cited by examiner

PAIRING OR ASSOCIATING ELECTRONIC DEVICES

FIELD

The present invention relates to establishing a communications link between electronic devices. In one aspect, it relates to a method of establishing pairing between an implanted medical device and a remote electronic device.

PRIORITY

The present application is a U.S. national stage application of International Application Serial No. PCT/IB2011/002545 filed Oct. 26, 2011, which claims priority to Australian Provisional Patent Application No. 2010904833 filed on Oct. 29, 2010, the contents of which are hereby incorporated by reference.

BACKGROUND

Examples of the present invention will be described in the context of pairing or associating a sound processor of a cochlear implant system with a remote electronic device, such as an external controller. However, the present invention should not be considered as being limited to this exemplary field of use.

Auditory prostheses include any acoustic or electrical auditory prosthesis, such as hearing aids, middle ear implants, cochlear implants, brain stem implants, auditory mid-brain implant, and other devices which provide electrical and/or acoustic stimulation to a recipient to assist with hearing. Such prostheses require an input in the form of an electrical signal that corresponds to a sound signal for processing by the prosthesis. The input is typically obtained from a microphone that receives a sound signal. For example, a conventional cochlear implant consists of an external part containing a microphone, sound processor, and a headpiece coil, and an implanted part, which contains an implant coil and a stimulator device coupled to an electrode array.

Sound is received at the microphone, which generates an electrical signal that is delivered to the sound processor as an input. The sound processor processes the input signal and generates control signals, according to a pre-defined sound processing strategy, for controlling the stimulation of the electrode array of the stimulator device. The control signals are transferred over a transcutaneous link by the headpiece coil via the implant coil to the stimulator device, which sends corresponding stimuli to appropriate electrodes of the electrode array that stimulate the recipient's auditory nerve to give a perception of hearing.

Bilateral auditory prosthesis systems exist. For example, a prosthesis may be fitted to both the right ear and left ear of a recipient to form a bilateral system. Each device in a bilateral system may operate independently of the other, or they may communicate by either a wireless or a wired connection in delivering joint assistance to the recipient.

From time to time it may be desirable to connect a component of such a system (e.g. the sound processor) to a remote electronic device, such as a remote control, computer, or other sound processor, to enable communication between them (e.g. to perform diagnostic tests on the processor, adjust settings, etc.). For example, the Cochlear™ Nucleus® CP810 Sound Processor can be wirelessly associated with a Nucleus® CR110 Remote Assistant (both manufactured by Cochlear Limited) to enable a recipient or other person using the Remote Assistant to easily monitor, control, and manage the operation of the sound processor and the cochlear implant generally.

The process for establishing communication between a sound processor and a remote electronic device is typically initiated by a user navigating a menu on the device and pressing the required control button. This process requires users to learn how to correctly initiate the pairing of the devices, which some people may find complicated.

Enabling one device to establish data communications with another device without the user initiating the pairing can run the risk that devices pair in unintended ways. In some cases of use, formation of unintended pairs is merely an inconvenience, but in others it may be a critical problem because the incorrect external device may obtain control of the auditory prosthesis.

Accordingly, it would be advantageous to have a method of pairing a component of an auditory prosthesis and a remote electronic device that provides ease of use and maintains security, or at least provides an alternative mechanism to existing techniques.

SUMMARY

In broad concept, the present invention provides a system that includes a first electronic device having a capacity to conduct communications on two channels to establish an association with a second electronic device. In certain embodiments, the first electronic device is an auditory prosthesis, and the second electronic device is a remote electronic device used for communicating with the auditory prosthesis. Embodiments of the present invention also encompass the second electronic device and the combination of the two devices together. In certain embodiments, the auditory prosthesis is a left or a right ear auditory prosthesis and the remote electronic device may be adapted to communicate with the left prosthesis and the right prosthesis so as to establish an association with both. The present invention also broadly relates to a method of establishing such associations.

In some embodiments, the system and method can be operated without requiring user input to begin the association. In other embodiments, the method may include some user control, for example requiring a button to be pressed to initiate or complete an association.

Accordingly, from one perspective, the invention broadly relates to a method of establishing a communications link between a first electronic device and a second electronic device. In one embodiment, the method includes communicating over a first communications channel between an auditory prosthesis and a remote electronic device and communicating over a second communications channel between the auditory prosthesis and the remote electronic device. The first communications channel is a short range or near field channel used to initiate a communications link, and the second communications channel is a broadcast channel to communicate over the communications link. The communications link is only established if communications over both the first and second channels are completed. The method also includes the auditory prosthesis and the remote electronic device exchanging at least one identifier for the communications link.

The auditory prosthesis may be an external component of a cochlear implant adapted to establish a communications link with an implant component of the cochlear implant. The auditory prosthesis may therefore include a sound processor and a communications system adapted to transmit signals over a short range or near field channel for controlling stimulation of an electrode array of a cochlea stimulator device. In some embodiments, the auditory prosthesis is configured to only allow establishment of a communications link with a remote electronic device when a communications link is not established with an implant component of the cochlear implant.

The first communication channel may, for example, be a 5 MHz inductive coupling link, and the second communication channel may be a broadcast channel, for example a 2.4 GHz radio frequency link. The first channel may have a range as short as 10 millimeters or less. The second channel may have a range of up to 10 meters. In other embodiments, the second channel may have a shorter range, anywhere down to about 100 millimeters. The auditory prosthesis and the remote electronic device may further communicate over the first channel subsequent to the remote electronic device sending the response over the second communication channel to confirm the communications link. In this way, devices that send a response over the second communication channel that are outside the range of the first communication channel do not establish a link with the auditory prosthesis.

In addition to the method described above, the invention extends to an implanted medical device, such as an auditory prosthesis, and to an electronic device adapted in hardware, firmware, and/or software to perform the method.

DRAWINGS

Figure 5:
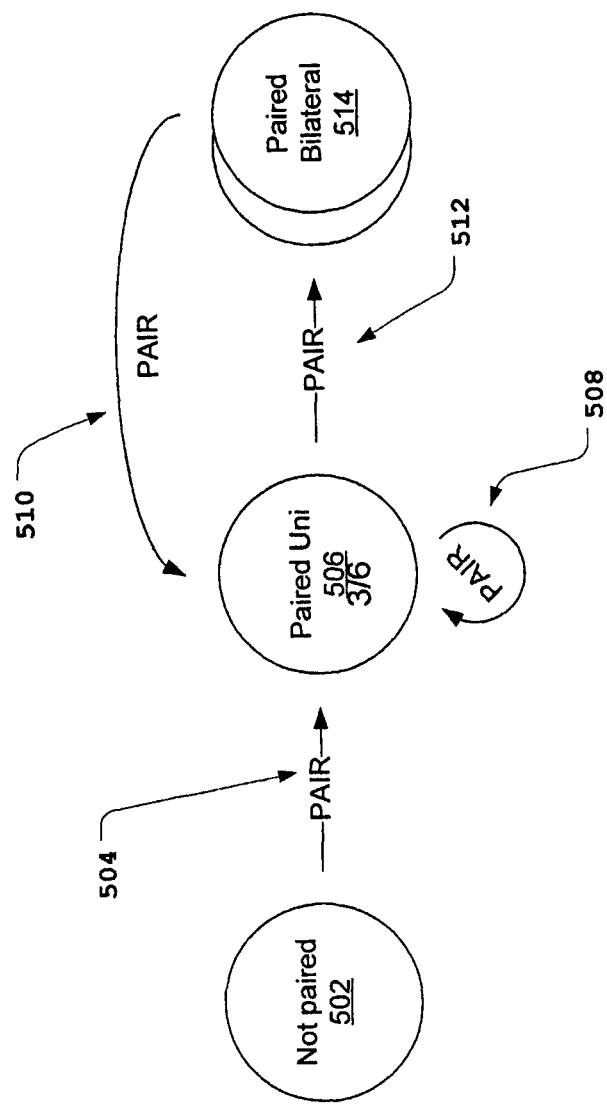
Figure 6A:
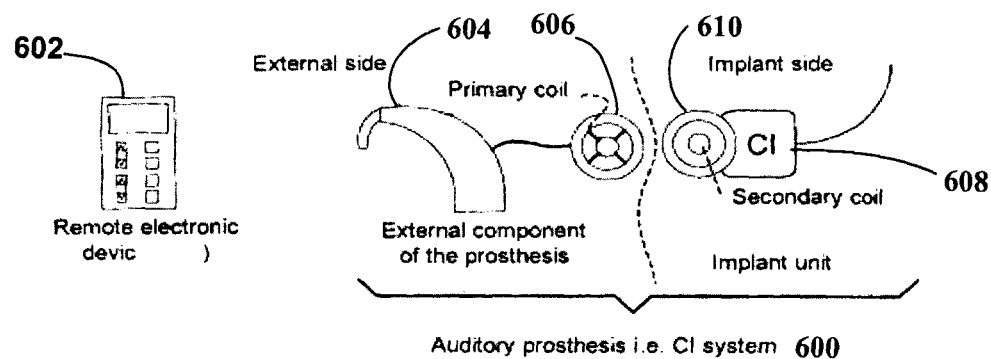
Figure 6B:
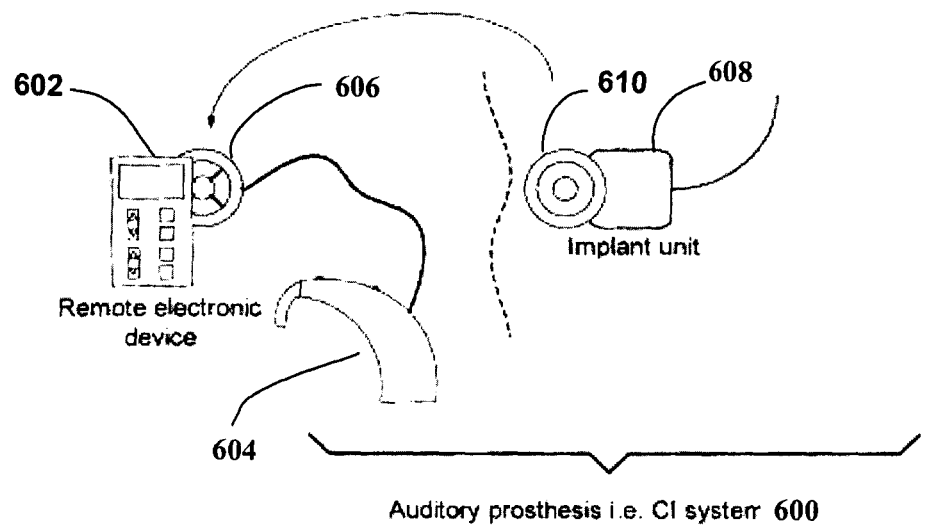

FIG. 5 is a schematic representation of a pairing management architecture for a remote electronic device and an auditory prosthesis in accordance with an embodiment of the present invention; and FIGS. 6A and 6B represent configurations of an auditory prosthesis that may control pairing or association of a remote electronic device with an auditory prosthesis in accordance with an embodiment of the present invention.

DETAILED DESCRIPTION

Illustrative embodiments of the present invention will now be described in the context of the formation of an association between a sound processor forming part of a cochlear implant and an external controller. However, embodiments of the invention can be applied generally to implanted medical devices, such as a pacemaker or implantable cardioverter-defibrillator. Therefore, aspects of the invention should not be considered as being limited to the field of application of the illustrative embodiments described herein.

Figure 1:
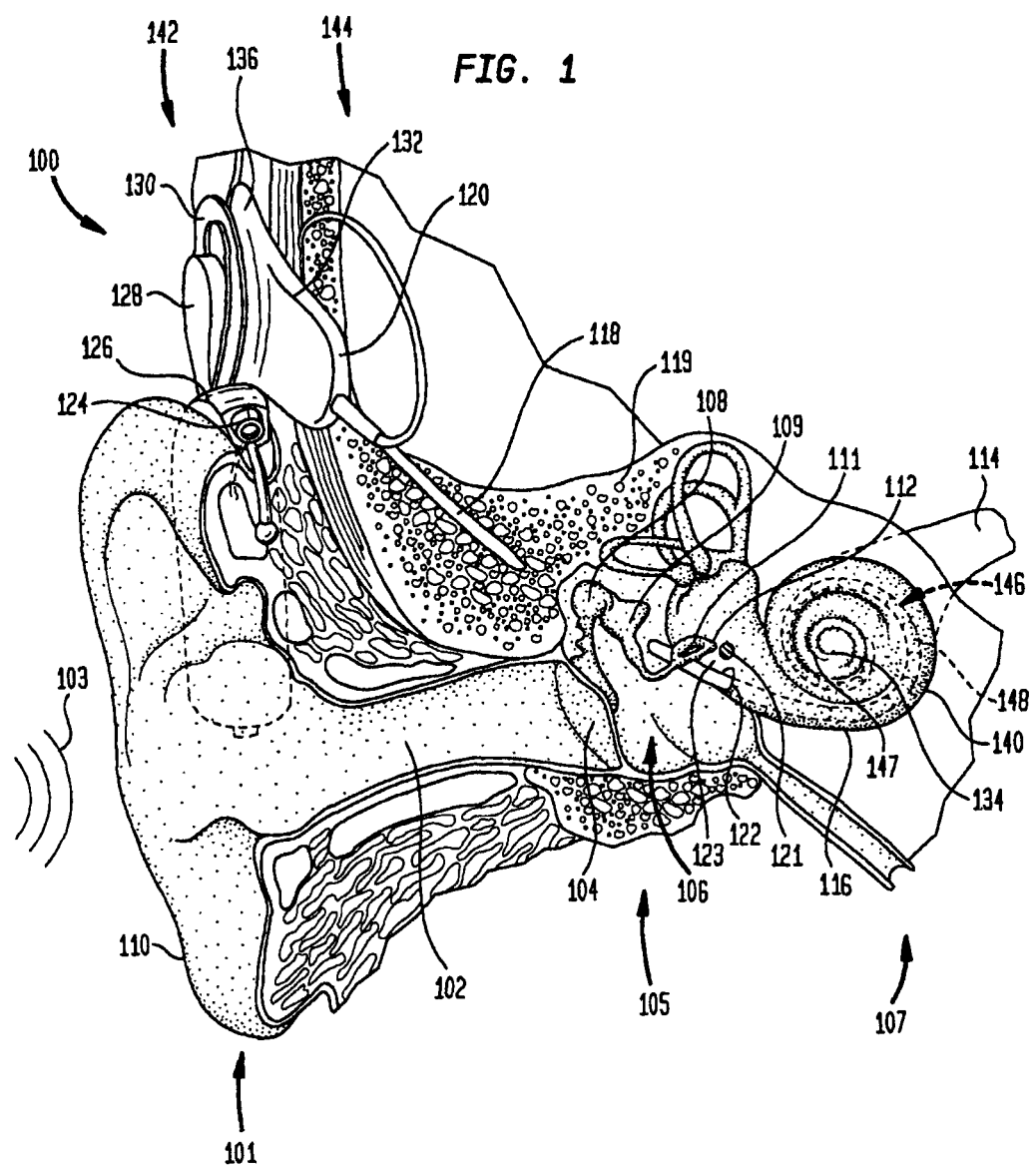
FIG. 1 is a perspective view of a cochlear implant for implant in a recipient, which may be used in an embodiment of the present invention.

FIG. 1 is a perspective view of a cochlear implant system 100, implanted in a recipient having an outer ear 101, a middle ear 105, and an inner ear 107. Components of outer ear 101, middle ear 105, and inner ear 107 are described below, followed by a description of cochlear implant system 100.

In a fully functional ear, outer ear 101 includes an auricle 110 and an ear canal 102. An acoustic pressure or sound wave 103 is collected by auricle 110 and is channelled into and through ear canal 102. Disposed across the distal end of ear canal 102 is tympanic membrane 104, which vibrates in response to the sound wave 103. This vibration is coupled to fenestra ovalis (or oval window) 112 through the three bones of middle ear 105, collectively referred to as ossicles 106 and including malleus 108, incus 109, and stapes 111. Bones 108, 109, and 111 of middle ear 105 serve to filter and amplify sound wave 103, causing fenestra ovalis 112 to articulate, or vibrate, in response to the vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant system 100 includes external component 142, which is directly or indirectly attached to the body of the recipient, and implant component 144, which is temporarily or permanently implanted in the recipient. External component 142 typically includes: one or more sound input elements, such as microphone 124 for detecting sound; sound processing unit 126; a power source (not shown); and external headpiece coil unit 128. External headpiece coil unit 128 includes external coil 130, which is circular in shape, and, preferably, a magnet (not shown) secured directly or indirectly to external coil 130. Sound processing unit 126 processes the output of microphone 124 that is positioned, in the depicted embodiment, adjacent to auricle 110 of the recipient. Sound processing unit 126 generates encoded signals, which are provided to external headpiece coil unit 128 via a cable (not shown).

Implant component 144 includes implant coil 136, stimulator unit 120, and elongated electrode assembly 118. Implant coil 136 includes, preferably, a magnet (not shown) fixed relatively concentric to the implant coil. Implant coil 136 includes an internal coil (not shown), and, preferably, a magnet (also not shown) fixed relative to the internal coil. Stimulator unit 120 is hermetically sealed within biocompatible housing 132, sometimes collectively referred to as the implant unit. The internal coil receives power and stimulation data from external coil 130, as noted above. Elongated electrode assembly 118 has a proximal end connected to stimulator unit 120, and a distal end implanted in cochlea 140. Elongated electrode assembly 118 extends from stimulator unit 120 to cochlea 140 through mastoid bone 119 and is implanted into cochlea 140. In some embodiments, electrode assembly 118 may be implanted at least in basal region 116, and sometimes further in cochlea 140. For example, elongated electrode assembly 118 may extend towards the apical end of cochlea 140, referred to as cochlear apex 134. In certain circumstances, elongated electrode assembly 118 may be inserted into cochlea 140 via cochleostomy 122. In other circumstances, a cochleostomy may be formed through round window 121, fenestra ovalis 112, promontory 123, or through an apical turn 147 of cochlea 140.

Elongated electrode assembly 118 includes electrode array 146 which further includes a series of longitudinally aligned and distally extending electrodes 148, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals that are applied by electrodes 148 to cochlea 140, thereby stimulating auditory nerve 114.

Because the cochlea is tonotopically mapped, that is, partitioned into regions each responsive to stimulus signals in a particular frequency range, each electrode of electrode array 146 delivers a stimulating signal to a particular region of the cochlea. In the conversion of sound to electrical stimulation, frequencies are allocated to individual electrodes of electrode assembly 118 that lie in positions in cochlea 140 that are close to the region that would naturally be stimulated in normal hearing. This enables the prosthetic hearing implant to bypass the hair cells (not shown) in cochlea 140 to directly deliver electrical stimulation to auditory nerve fibers (not shown), thereby allowing the brain (not shown) to perceive hearing sensations resembling natural hearing sensations. In achieving this, processing channels, that is, specific frequency bands with their associated signal processing paths, of sound processing unit 126 are mapped to a set of one or more electrodes to stimulate a desired nerve fiber or nerve region of cochlea 140. Such sets of one or more electrodes used for stimulation are referred to herein as "electrode channels" or "stimulation channels."

In cochlear implant system 100, external coil 130 transfers electrical signals (i.e., power and stimulation data) to internal coil 136 via an inductive RF link. Internal coil 136 is a closed loop wire antenna coil of multiple turns of electrically insulated single-strand or multi-strand platinum or gold wire. The electrical insulation of internal coil 136 is provided by a flexible silicone molding (not shown). In use, biocompatible housing 132 may be positioned in a recess of the temporal bone (not shown) adjacent to auricle 110 of the recipient.

Cochlear implant system 100 of FIG. 1 may be used in bilateral implant systems. For example, in some embodiments, cochlear implant system 100 may be fitted to both the right ear and left ear of a recipient to form a bilateral implant system. In such a bilateral system, these cochlear implants may operate independently of one another, or they may communicate by either a wireless or a wired connection in delivering joint stimulation to the recipient.

Figure 2:
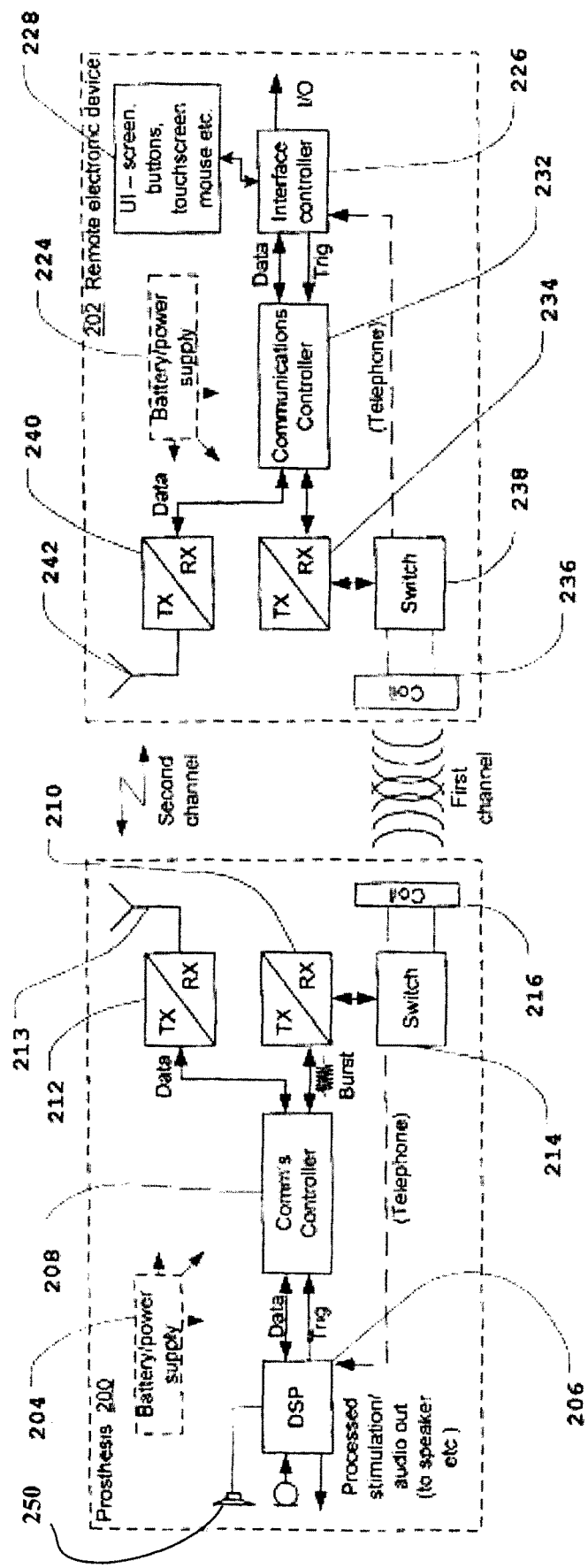
FIG. 2 illustrates schematically an auditory prosthesis and a remote electronic device, which can be paired using a method according to an embodiment of the present invention.

As discussed above, it may be necessary or desirable to establish a communications link with cochlear implant system 100. This is most conveniently done using a wireless communications link. FIG. 2 is a block diagram showing components of an implantable medical device, such as the cochlear implant system illustrated in FIG. 1, that are used in forming a communications link with a second, external device.

FIG. 2 illustrates an electrical block schematic of auditory prosthesis 200 and remote electronic device 202. Auditory prosthesis 200 may include an external component connectable to an implant unit or may be another device, such as a hearing aid. Remote electronic device 202 could be a controller configured to interface with auditory prosthesis 200, or another electronic device that needs to communicate with auditory prosthesis 200. In the embodiment shown in FIG. 2, auditory prosthesis 200 is an external component connectable to implant unit 250. Implant unit 250 may be implant component 144 as described above. In particular, auditory prosthesis 200 may be a mostly implantable cochlear implant, which includes both external and internal components substantially as described above, or a totally implantable cochlear implant, in which all the external components described with reference to FIG. 1 are implanted internally.

Battery or power supply 204 delivers power to the components of auditory prosthesis 200. In the present embodiment, signal processor 206 is a digital signal processor (DSP), which includes, depending on the particular implementation, interfaces to input and output systems. For example, signal processor 206 may interface to one or more microphones and/or interface to one or more outputs, such as a speaker and/or data port. Auditory prosthesis 200 also includes communications controller 208, which is connected to first transceiver 210 and second transceiver 212. First transceiver 210 is configured to transmit and receive data signals on a first communications channel, and second transceiver 212 is configured to transmit and receive on a second communications channel.

The first communications channel is preferably a short range or near field communications channel. In this example, the first communications channel is a 5 MHz, near field communications channel. Accordingly, auditory prosthesis 200 includes switch 214 and RF coil 216, which is in the form of a circular coil. In some embodiments, RF coil 216 is external coil 130 (or primary coil) described above. In other words, auditory prosthesis 200 uses RF coil 216 for pairing with the remote electronic device and communicating (including transferring power) with the implant component of the cochlear implant. In different embodiments, the first communications channel may have a different frequency selected from within the range of 9 kHz to 30 MHz (inclusive). The arrangement of using a single coil for communications with both implant unit 250 and remote electronic device 202 is illustrated in FIG. 2.

In the case of a totally implantable cochlear implant, both external coil 130 and RF coil 216 are internally implanted coils that are able to communicate with external devices, such as remote electronic device 202.

Switch 214 is used to select the manner in which received signals are routed through auditory prosthesis 200 (e.g. directly to the signal processor 206 or via communications controller 208). This provides additional flexibility for the purposes of implementing a wider range of functions and methods of processing that may not be related to the pairing process. Accordingly, in other embodiments, switch 214 can be omitted from prosthesis 200 and corresponding switch 238 may also be omitted from the remote electronic device 202.

Second transceiver 212 may be a radio frequency transceiver adapted to communicate wirelessly with another device, for example at 2.4 GHz. Second transceiver 212 is coupled to a suitable antenna, depicted in FIG. 2 as antenna 213. Second transceiver 212 and antenna 213 may have a range of up to about 10 m. However, in other embodiments, a transceiver and an antenna with a lower range may be used; for example, transceiver 212 and an antenna 213 may have ranges of about 2 m to 5 m. Due to physical constraints in the present embodiment on the location of antennas 213, 242, the minimum range is about 10 cm to 15 cm. Shorter ranges may reduce the reliability of the communications link, whereas longer ranges may consume more power and may increase the risk of inadvertent or incorrect pairing. Accordingly, the currently preferred range is between about 0.5 m to about 1 m. However, other technologies may provide ranges that are larger or smaller, which could be used with this invention. Second transceiver 212 of auditory prosthesis 200 and second transceiver 240 of remote electronic device 202 may accordingly have a power within the range of about −20 dBm to about −15 dBm. In other embodiments, with longer and shorter ranges, the power may be within the range of about −25 dBm to about 0 dBm. In still other embodiments, the second communications channel has another frequency selected from within the range of 30 MHz to 11 GHz (inclusive).

In some embodiments, the first and second communications channels are selected to have different frequency bands. However, in other embodiments there may be an overlap in frequencies, in which case the communication protocols may be different so as to distinguish communications across the two channels.

Battery or power supply 224 provides power to remote electronic device 202. The functions of remote electronic device 202 are controlled by controller 226, for example, a digital signal processor or a microprocessor. Additionally, interface controller 226 is coupled to user interface 228. User interface 228 could be any known type of interface, such as a screen, touch screen, keyboard, mouse, series of buttons, or any other user input device. Remote electronic device 202 may also include an additional input or output mechanism to enable connection to other devices or systems. In some embodiments, those other devices or systems may provide an expanded or different user interface; for example, where the other device is a desktop computer running an application for communicating with remote electronic device 202. Communications with auditory prosthesis 200 are controlled by the communications controller 232.

Remote electronic device 202 includes first transceiver 234 for communicating on a first communications channel. Accordingly, auditory prosthesis 202 includes RF coil 236, which in this embodiment is in the form of an inductive closed loop, to communicate with RF coil 216. Switch 238 is also provided.

Second transceiver 240 is provided for communicating on the second communications channel. Second transceiver 240 is coupled to antenna 242 and is adapted for transmitting radio frequency signals (e.g. at 2.4 GHz). Although this example indicates that remote electronic device 202 is capable of transmitting on the first communications channel, this may not be the case in some embodiments. Accordingly, first transceiver 234 of remote electronic device 202 may be a receiver only.

It should be understood that the present example is described as having a radio frequency channel based upon electromagnetic (EM) field propagation (e.g. 2.4 GHz) and near field magnetic inductive (MI) coupling (e.g. 5 MHz). However, the present invention could also be implemented with other physical communications methods. For example, either or both communications channels could use other parts of the EM or MI spectrum for establishing communication channels, such as microwave, optical (e.g. infrared or ultraviolet), or acoustic channels (e.g. using ultrasonic waves). As will be described below, the two communications channels have different roles in the communications process. The first communications channel plays the role of initiating communications and transmitting confirmation signals between the implanted medical device and remote electronic device. The second communications channel is used for data transmission purposes during the establishment of the communications link and for communications over the link itself. In some embodiments, the first communications link is operable over a distance of up to 3 meters. In other embodiments the first communications link is operable over a distance of approximately 2 m, down to 0.5 m or even less than 1 cm. As will be seen from the following description, utilizing a short range channel, which may be 0.5 cm or less, can have certain advantages in preventing unwanted pairing between devices.

Figure 3:
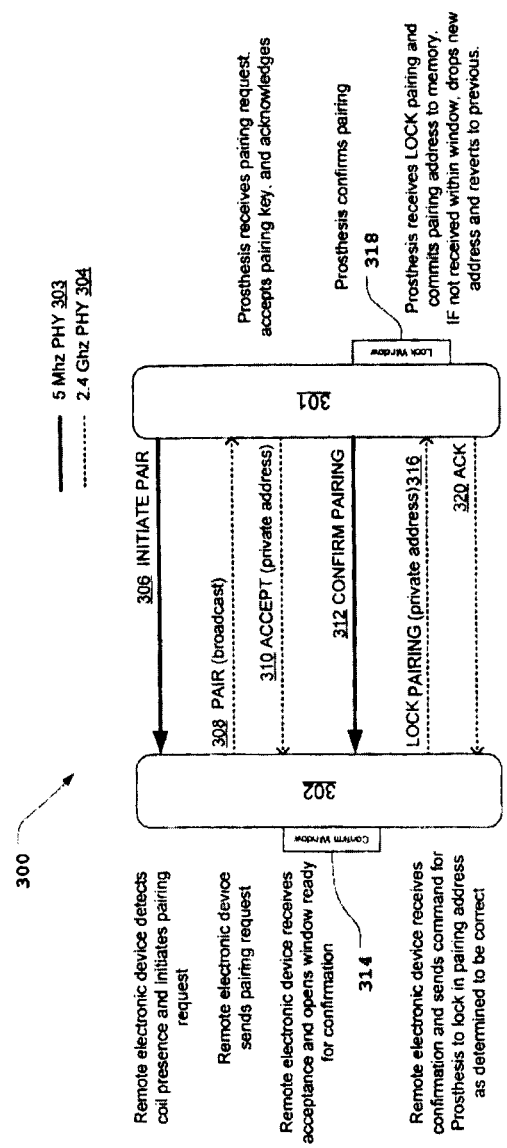
FIG. 3 is a flow-chart illustrating a method for initiating establishment of a communications association between an auditory prosthesis and remote electronic device in accordance with an embodiment of the present invention.

FIG. 3 illustrates method 300 for establishing the communications link by pairing two devices. In FIG. 3, the devices are referenced as auditory prosthesis 301 and remote electronic device 302. These may have the internal structure described for the corresponding components in FIG. 2. Method 300 is an asynchronous communications procedure between the two devices over two channels.

Prior to the beginning of method 300, a user (who may or may not have an implanted medical device, such as auditory prosthesis 301) wishing to pair the devices places them sufficiently close together so that communication can take place across both the first and second communications channels. In the illustrated embodiment, the first communications channel is a near field communications link established using the first transceiver of auditory prosthesis 301 and the first transceiver of remote electronic device 302, as illustrated in FIG. 2. Accordingly, remote electronic device 302 and auditory prosthesis 301 need to be relatively positioned such that the near field communications mechanisms will operate.

In embodiments where auditory prosthesis 301 has an external component and an implant unit, auditory prosthesis 301 intermittently transmits or continually activates on the first communications channel. In these embodiments, the first communications channel may include: a power signal, which may be power frames or a modulated power signal, for powering up the implant component of the implant; and data, which may be stimulation or sound signals. Either of these types of signals may be used to initiate pairing. Use of the power signal alone will be suitable for many embodiments.

Because auditory prosthesis 301 activates on the first communications channel intermittently or continually, and as a result of implementing method 300, all a user needs to do to initiate pairing with the remote electronic device is bring them into sufficiently close proximity that a signal transmitted on the first communications channel by auditory prosthesis 301 can be received by remote electronic device 302. In some embodiments, no other user initiation of the system is necessary. In other embodiments, user input may be required; for example, a button on the external device may need to be depressed before step 308 (see below) is initiated.

In some embodiments where auditory prosthesis 301 is a cochlear implant including an external component and implant unit 250 (see FIG. 2), the pairing method is only performed if the external component of auditory prosthesis 301 is not communicably connected to the implant component of the cochlear implant. This is achieved by monitoring for telemetry received by auditory prosthesis 301 back from the internal implant through coil 216. For example, auditory prosthesis 301 may only perform step 310 in FIG. 3 if it is not receiving telemetry from an implant component of the cochlear implant in response to the power signal auditory prosthesis 301 is transmitting on the first communications channel. In other words, to avoid situations of cross-pairing or false associations, the external component of auditory prosthesis 301 automatically disables the function for transmit ACCEPT signals once the implant component of the auditory prosthesis is powered. In this case, auditory prosthesis 301 will not confirm pairing. Accordingly, when the primary coil or headpiece coil unit of external component of the prosthesis (see also coil 128 of FIG. 1) is connected to the secondary coil of the implant component of the prosthesis (see also coil 136 of FIG. 1) as in normal operation mode, the prosthesis cannot be paired with any remote electronic device.

This method is illustrated in FIGS. 6A and 6B. In the embodiment illustrated in FIG. 6A, external component 604 of auditory prosthesis 600, which may be in the form of a cochlear implant 100, is coupled to implant component 608 of auditory prosthesis 600, as determined through primary coil 606 of external component 604 and secondary coil 610 of implant component 608, as explained above. Remote electronic device 602 and auditory prosthesis 600 will not pair when in this configuration. Remote electronic device 602 and auditory prosthesis 600 can only pair when in the uncoupled configuration shown in FIG. 6B and will remain paired during operation of the cochlear implant or other implanted medical device.

Returning to method 300 represented in FIG. 3, the method includes communications over the following two channels:
a first communications channel 303 that is a short range or near field communications link; e.g. a channel formed by inductive coupling, modulated at around 5 MHz, which is indicated in FIG. 3 by solid lines; and
a second communications channel 304 that is a broadcast channel or a channel with an address known by all devices (i.e. both remote electronic device 302 and auditory prosthesis 301); in this embodiment, second communications channel 304 is a wireless radio frequency channel modulated at around 2.4 GHz, which is indicated in FIG. 3 by dotted lines.

In first step 306, the external component of auditory prosthesis 301 transmits an INITIATE PAIR signal on first communications channel 303, and the signal is received by remote electronic device 302. Remote electronic device 302 responds in step 308 by transmitting a PAIR signal on second communications channel 304. The PAIR signal in step 308 is a broadcast transmission that will be receivable by any other device within range. In response to receiving the PAIR signal, auditory prosthesis 301 accepts the request to pair with remote electronic device 302 and, in step 310, transmits an ACCEPT signal, which includes a unique identifier such as a key or address for the communications link over second communications channel 304.

The unique identifier of the external component of auditory prosthesis 301 may be stored in hardware or firmware readable by communications controller 208, as shown in FIG. 2. This identifier is used to identify/address communications between remote external device 302 and auditory prosthesis 301 after pairing has been completed. For example, the unique identifier may be placed in the headers of data packets transmitted between the devices.

In other embodiments, the unique identifier for the communications link may be sourced from remote electronic device 302 or from the implant component of auditory prosthesis 301, instead of the external part of auditory prosthesis 301. For example, where the unique identifier is sourced from remote electronic device 302, the unique identifier may be transmitted in step 308, and in step 310 the prosthesis may return the same identifier to accept the pairing. Where remote electronic device 302 is to pair with a plurality of prostheses, it may have a corresponding plurality of unique identifiers. In still other embodiments, the unique identifier for a communications link may be a combination of the unique identifiers formed by an identifier for auditory prosthesis 301 and an identifier for remote electronic device 302, such as a serial amalgamation of the identifiers.

In step 312, the external component of auditory prosthesis 301 confirms the pairing request by transmitting a CONFIRM PAIRING signal on first communications channel 303. Upon receipt of the ACCEPT signal, remote electronic device 302 opens confirm window 314. If the confirm window 314 expires before remote electronic device 302 receives the CONFIRM PAIRING signal sent by auditory prosthesis 301 in step 312, remote electronic device 302 will determine that pairing has not succeeded (this process will be described further in connection with FIG. 4). In response to the receiving the CONFIRM PAIRING signal transmitted in step 312 prior to the expiration of confirm window 314, remote electronic device 302 will transmit a LOCK PAIRING signal in step 316 to auditory prosthesis 301 using second communications channel 304, which will confirm the unique identifier associated with the communications link being established.

After transmitting the CONFIRM PAIRING signal in step 312, the external component of auditory prosthesis 301 will open lock window 318. If the external component of auditory prosthesis 301 does not receive the LOCK PAIRING signal transmitted in step 316 before the expiration of lock window 318, the external component of auditory prosthesis 301 will abort the pairing process and cancel the identifier associated with the channel being established. If the external component of auditory prosthesis 301 receives the LOCK PAIRING signal transmitted in step 316 prior to the expiration of lock window 318 and the unique identifier in the LOCK PAIRING signal matches the unique identifier transmitted in step 310, it transmits an ACK signal in step 320 using second communications channel 304. Upon remote electronic device 302 receiving the ACK signal, the communications link is established and communications can proceed on second communications channel 304.

Figure 4:
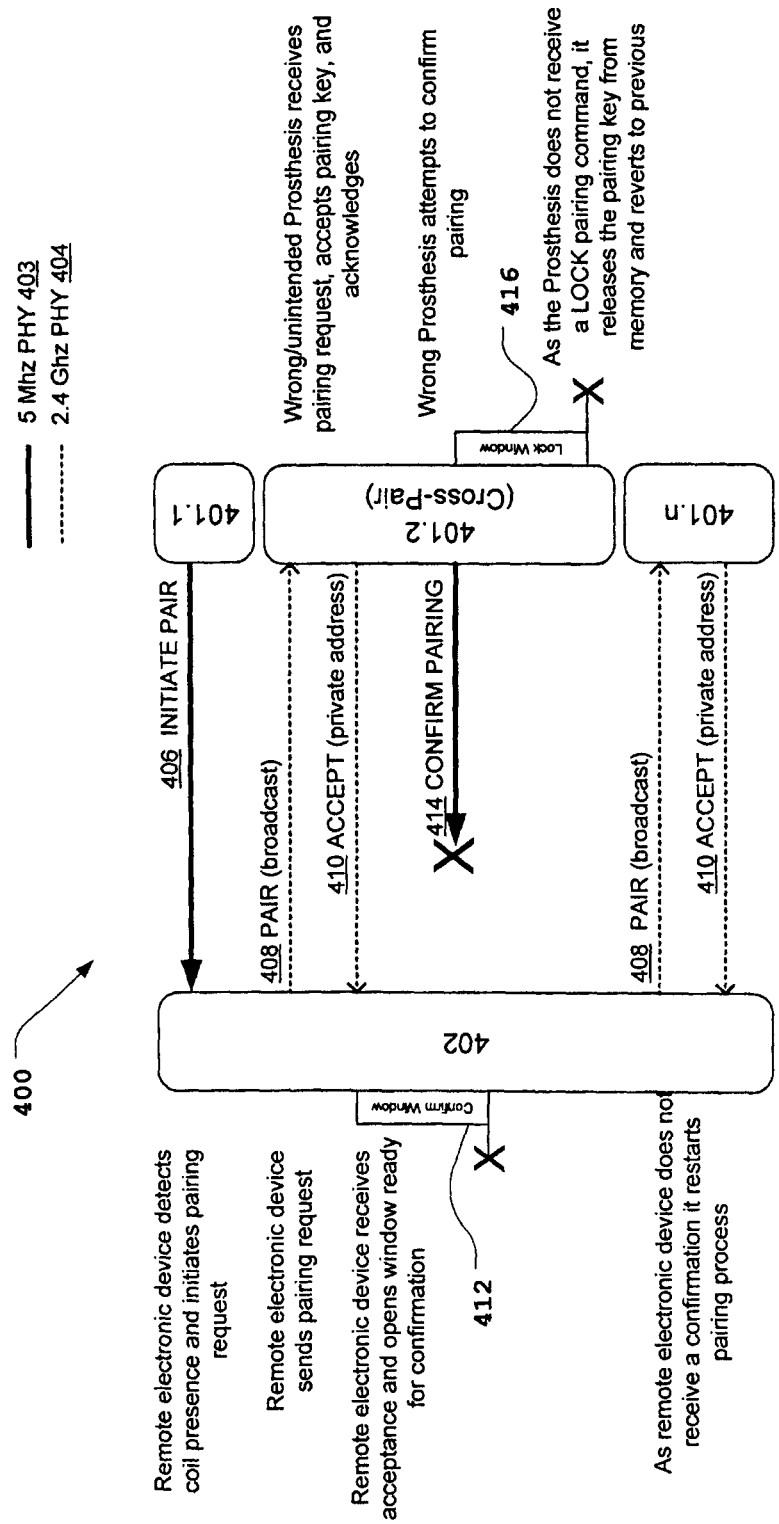
FIG. 4 is a flow-chart illustrating an example of the method of FIG. 3 that fails to result in the formation of an association between two devices because an additional device attempts to complete the pairing initiated by the auditory prosthesis.

FIG. 4 illustrates method 400 similar to that of FIG. 3, except that FIG. 4 illustrates the case in which multiple auditory prostheses attempt to pair with the same remote electronic device. In this example, there is illustrated auditory prosthesis 401.1, second auditory prosthesis 401.2, nth auditory prosthesis 401.n, and remote electronic device 402. As previously described, in the preferred embodiment first communications channel 403 is a near field communications channel, and second communications channel 404 is a longer range channel. As described in connection with FIG. 3, pairing is initiated in step 406 by auditory prosthesis 401.1 transmitting an INITIATE PAIR signal on first communications channel 403. This message is received by remote electronic device 402, and in response remote electronic device 402 broadcasts a PAIR signal on second communications channel 404. In the present case, second auditory prosthesis 401.2 receives the PAIR signal. This may occur because the second communications channel has a relatively long range compared with the first channel. Accordingly, an unintended auditory prosthesis has received the PAIR signal and, in response, generates a unique identifier. In step 410, second auditory prosthesis 401.2 transmits an ACCEPT signal, which contains the unique identifier, on second communications channel 404.

As was the case in FIG. 3, remote electronic device 402 receives the ACCEPT signal transmitted by second auditory prosthesis 401.2 and opens confirm window 412. However, because second auditory prosthesis 401.2 was not intended to be paired with remote electronic device 402, it is likely that it will be out of range for communication via first communication channel 403. Thus, when it sends a CONFIRM PAIRING signal in step 414, the signal is not received by remote electronic device 402. Accordingly, confirm window 412 expires without receiving a CONFIRM PAIRING signal. Since remote electronic device 402 has determined that the pairing process has failed, it will not transmit a lock pairing command. Therefore, lock window 416 opened by second auditory prosthesis 401.2 will expire without receiving a LOCK PAIRING signal, and second auditory prosthesis 401.2 will determine that the pairing has been unsuccessful.

Remote electronic device 402, upon failure of the initial attempt at forming an association with the first auditory prosthesis 401.1, will return to the state in which it may send a request for pairing and repeats step 408. If this transmission is received by an auditory prosthesis e.g. 401.n, the pairing process begins again.

Due to the communication protocol described above, implemented as an asynchronous non-session layer 1 protocol, discrete synchronization/pilot packets transmitted in steps 308, 408 are statistically unlikely to register with more than one external device for a given protocol window. Timing of the synchronization frames may be, for example, 64 msec apart and establish the subsequent timing of the payload packets within which the pairing request information is contained. As such, in practice, the protocol behaves such that the broadcast pairing request is received and acknowledged by either the intended device or the unintended device, but not both.

As can be seen from the above description of FIG. 4, the use of a near field channel for initiating the establishment of the communications link between the two devices takes advantage of the short transmission distance of that channel which advantageously prevents a pairing between unintended auditory prostheses and remote electronic devices.

FIG. 5 illustrates a schematic representation of the pairing management architecture of an embodiment of the present invention. In one embodiment, the method is able to be activated from any user interface of the remote electronic device and will not normally require the remote electronic device to actively unpair at any stage. The unpairing process performed by the remote electronic device will simply require overwriting the unique identifier or key associated with an established communications link in a memory of the remote electronic device. This is diagrammatically illustrated in FIG. 5, which shows first state 502 in which no pairing identifier is written to the memory of the remote electronic device. Upon completing of pairing process 504, the remote electronic device will write pairing address 506 to its memory. This address can be overwritten by re-establishing a communications link with the same auditory prosthesis in process 508 or pairing with a different auditory prosthesis in process 510.

Additionally, process 512 illustrates how, in some instances, the remote electronic device can be arranged to pair with more than one auditory prosthesis, as would be the case where a controller is paired with a left and a right ear auditory prosthesis of a bilateral cochlear implant system to achieve state 514. The pairing is performed in series. In some embodiments, auditory prosthesis 200 includes in firmware or hardware an identification of whether it is a left ear or a right ear auditory prosthesis and communicates this to the remote electronic device, for example, in step 310 of FIG. 3.

In some embodiments, the remote electronic device is configured to pair with only one left ear auditory prosthesis and only one right ear auditory prosthesis. For example, if it has paired with a left ear auditory prosthesis and the transmission received from an auditory prosthesis in step 310 (or at another stage of the process) indicates that the prosthesis is a left ear auditory prosthesis, then, if the pairing process is successful, the previous pairing identifier for the left ear auditory prosthesis will be overwritten. The same check may occur for a right ear auditory prosthesis.

In other embodiments, the remote electronic device is configured to pair with more than one left ear auditory prosthesis and more than one right ear auditory prosthesis. In these embodiments, the external device may distinguish between prostheses by a serial number or other identifier of the prosthesis.

Various alternative implementations of parts of the processes as described herein may be applied in certain embodiments of the present invention. For example, the implanted medical device and/or remote electronic devices could be configured such that either one or both of the devices requires a single button press to request pairing. This button press can be used either to initiate the method described in FIG. 3, or to confirm receipt of one of the earlier steps of the pairing request. Such a process preserves the security features of the present invention but gives users a sense of control over the pairing of their devices.

In the illustrative embodiments described herein, the transmissions on the first communications channel are simply a single pulse or bit of information being transmitted across the short range or near field channel such that closed loop communications across the channel exist. However, more complex transmissions can be performed across the short range or near field channel in some implementations of the present invention. For example, a first identifier can be transmitted across the short range or near field channel, which can then be confirmed with one or more of the subsequent transmissions on the second communications channel. This provides an additional check against unintended associations. Alternatively, the first exchange of identifiers may occur on the second communications channel (i.e. in step 308 and/or step 310 in FIG. 3) and a confirmatory exchange performed on the first communication channel (i.e. in step 312 in FIG. 3). In some implementations of these embodiments, the identifier communicated using the short range or near field channel may be the same as the identifier communicated using the second communications channel.

In some embodiments, the identifier communicated via the short range or near field channel may be the identifier used for communications between the devices after pairing. In other words, in some embodiments as described previously herein, the exchange of an identifier occurs over the second communications channel (the broadcast channel) only. In other embodiments, the exchange utilizes both the first and second communications channels, and in still other embodiments, the exchange is effected using the first communications channel (the short range or near field channel) only.

Where only the short range or near field channel is used to exchange identifiers, for example by sending an identifier in step 312 of FIG. 3, then steps 308 and 310 may omit exchanging any identifier. These steps may involve transmitting a simple pulse or similar signal to establish that there is a connection on the second communications channel.

The embodiments described herein use a near field EM coupling for the first communications channel. However, it should be appreciated that any channel that is relatively short range may be used for the transmissions on the first communications channel. For example, ultrasonic or light based channels may be used for the first or second communications channels as alternatives to the other communications channels described herein.

The auditory prosthesis embodiments described herein have been described primarily with reference to an auditory prosthesis such as a cochlear implant. The method described with reference to FIGS. 3 and 4 takes advantage of the primary coil connected to the external component of the prosthesis. In other embodiments, the remote electronic device may initiate the pairing. In other words, the remote electronic device may intermittently or continually transmit a signal on the first communications channel, which is received by the external component of the prosthesis to initiate pairing. Subsequent steps in the method may then be reversed, with step 308 being a transmission from the auditory prosthesis to the external device, and step 310 being an acceptance transmitted from the external device to the auditory prosthesis. Step 312 may then be a communication in either direction, or, in other embodiments, communication in both directions may be required to confirm the pairing. Steps 316 and 320 may similarly be reversed in transmission directions.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method comprising:
   initiating establishment of a communications link between a medical device and a remote electronic device by transmitting one or more signals from the medical device to the remote electronic device over a first communications channel between the medical device and the remote electronic device; and
   establishing the communications link between the medical device and the remote electronic device by communicating over the first communications channel and a second communications channel between the medical device and the remote electronic device, wherein
   a signal communicated over the second communications channel has a longer range than a signal communicated over the first communications channel, and
   at least one of communicating over the first communications channel or communicating over the second communications channel comprises exchanging between the medical device and the remote electronic device at least one identifier for the communications link,
   the medical device includes an external component of the medical device, and
   the medical device is configured such that the action of establishing the communications link between the medical device and the remote device is executed only if the external component is not communicably connected to an implanted component of the medical device.

2. A method as claimed in claim 1, wherein the initiation of the establishment of the communications link comprises:
   transmitting an initiate signal by the medical device; and
   receiving the initiate signal by the remote electronic device, and
   wherein the initiate signal is a power signal.

3. A method as claimed in claim 1, wherein establishing the communications link comprises:
   transmitting a pair request signal from the remote electronic device to the medical device over the second communications channel upon the medical device initiating the establishment of the communication link;
   receiving the pair request signal by the medical device;
   transmitting an accept signal by the medical device over the second communications in response to receiving the pair request signal;
   receiving the accept signal by the remote electronic device;
   transmitting a confirmation signal by the medical device;
   receiving the confirmation signal by the remote electronic device;
   determining whether the remote electronic device received the confirmation signal; and
   ending the establishment of the communications link in response to determining that the remote electronic device failed to receive the confirmation signal.

4. A method as claimed in claim 1, wherein the action of initiating the establishment of the communications link is executed without initiation by the recipient of the medical device.

5. A method as claimed in claim 1, wherein:
   the method further comprises establishing a communications link between an external component of the medical device and an implanted component of the medical device; and
   the action of initiating establishment of a communications link between the medical device and the remote device is established between the external component and the remote device.

6. A method as claimed in claim 1, further comprising:
   at least one of performing diagnostic tests on a processor of the medical device or adjusting a setting of the medical device using the communications link established between the medical device and the remote electronic device, wherein the medical device is a totally implantable medical device.

7. A method as claimed in claim 1, wherein the establishment of the communications link occurs without a recipient of the medical device providing input.

8. A method as claimed in claim 1, wherein the initiation the establishment of the communications link occurs as a result of a recipient of the medical device affirmatively initiating such.

9. A method as claimed in claim 1, wherein:
   the action of initiating establishment of a communications link between a medical device and a remote electronic device is executed using a first transmitter of the medical device;
   the method further comprises establishing a communications link between an external component of the medical device and an implanted component of the medical device using the first transmitter when the external component is in signal communication with the implanted component;
   the action of establishing the communications link between the medical device and the remote device occurs when the communications link between the external component and the implanted component is not present; and
   the action of establishing the communications link between the medical device and the remote device is permitted to occur only if the communications link between the external component and the implanted component is not present.

10. A method as claimed in claim 1, wherein
the first communications channel is one of a short range communications channel or a near field communications channel that has a frequency within a range of about 9 kHz to about 30 MHz.

11. A method as claimed in claim 1, wherein:
the method further comprises establishing a communications link between an external component of the medical device and an implanted component of the medical device; and
the action of initiating establishment of a communications link between the medical device and the remote electronic device is established between the external component and the remote electronic device and the method further comprises executing two way communications over the first communications channel and executing two way communications over the second communications channel.

12. A method as claimed in claim 1, wherein
the first communications channel is established using a component that has a transmission range of 10 mm or less and the second communications channel is established using a component that has a range of up to 10 meters.

13. A method as claimed in claim 1, wherein
the first communications channel is established using a component that has a transmission range limit that requires the medical device to be in the immediate vicinity of the remote electronic device.

14. A method comprising:
initiating establishment of a communications link between a medical device and a remote electronic device by transmitting one or more signals from the medical device to the remote electronic device over a first communications channel between the medical device and the remote electronic device; and
establishing the communications link between the medical device and the remote electronic device by communicating over the first communications channel and a second communications channel between the medical device and the remote electronic device, wherein
a signal communicated over the second communications channel has a longer range than a signal communicated over the first communications channel,
at least one of communicating over the first communications channel or communicating over the second communications channel comprises exchanging between the medical device and the remote electronic device at least one identifier for the communications link, and
the method further comprises:
establishing a second communications link between a second medical device including an implanted component and the remote electronic device by transmitting the one or more signals from the remote electronic device over the second communications channel, which also exists between the second medical device and the remote electronic device; and
not establishing a third communications link between the second medical device and the remote electronic device even though a signal is provided over the first communications channel by the second medical device, wherein
a signal communicated over the second communications link has a longer range than the signal provided over the first communications channel by the remote electronic device and has a range that is the same as the signal communicated over the second communications channel.

15. A method as claimed in claim 14, wherein
the first communications channel is one of a short range communications channel or a near field communications channel that has a frequency within a range of about 9 kHz to about 30 MHz; and
the second communications channel is a broadcast communications channel that has a frequency within a range of about 30 MHz to about 11 GHz.

16. A method as claimed in claim 14, wherein establishing the communications link comprises:
transmitting a confirmation signal by the medical device;
receiving the confirmation signal by the remote electronic device;
transmitting a lock signal by the remote electronic device in response to receiving the confirmation signal;
receiving the lock signal by the medical device;
determining whether the medical device received the lock signal; and
in response to determining that the medical device received the lock signal, transmitting an acknowledgement signal by the medical device via the second communications channel.

17. A method as claimed in claim 16, wherein a link identifier is embedded in the lock signal, and wherein determining whether the medical device received the lock signal includes determining that the link identifier matches the unique identifier stored in a memory of the medical device, and
wherein determining whether the medical device received the lock signal comprises determining whether the medical device received the lock signal within a time period that begins when the medical device transmits the accept signal.

18. A method as claimed in claim 16, wherein the method is executed such that the medical device and the remote device remain autonomous devices.

19. A method as claimed in claim 14, further comprising:
at least one of performing diagnostic tests on a processor of the medical device or adjusting a setting of the medical device using the communications link established between the medical device and the remote electronic device.

20. A method as claimed in claim 14, wherein the action of communicating over the first communications channel entails communicating utilizing near field magnetic inductive (MI) communication.

21. A method as claimed in claim 14, wherein the communications link is only established if communications over both the first and second channels are completed.

22. A method as claimed in claim 14, wherein:
the action of initiating establishment of a communications link between a medical device and a remote electronic device is executed using a first transmitter of the medical device; and
the first transmitter is implanted in the recipient.

23. A method as claimed in claim 14, wherein:
the method further comprises establishing a communications link between an external component of the medical device and an implanted component of the medical device; and
the medical device is configured such that when the external component has the established communication link with the implanted component, pairing between the medical device and the remote electronic device cannot take place.

24. A method as claimed in claim 14, wherein:

the method further comprises establishing a communications link between an external component of the medical device and an implanted component of the medical device; and the medical device is configured such that pairing between the medical device and the remote electronic device cannot take place when the medical device is in its normal operation mode.

\* \* \* \* \*